US00PP14804P2

(12) United States Plant Patent
Fear et al.

(10) Patent No.: US PP14,804 P2
(45) Date of Patent: May 18, 2004

(54) RASPBERRY PLANT NAMED 'DRISCOLL MARAVILLA'

(50) Latin Name: *Rubus idaeus L.*
Varietal Denomination: Driscoll Maravilla

(75) Inventors: Carlos D. Fear, Aptos, CA (US); Richard E. Harrison, Aptos, CA (US); Fred M. Cook, Aptos, CA (US); Gavin Sills, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 6 days.

(21) Appl. No.: 10/306,451

(22) Filed: Nov. 27, 2002

(51) Int. Cl.[7] ..... A01H 5/00
(52) U.S. Cl. ..... Plt./204
(58) Field of Search ..... Plt./204

*Primary Examiner*—Bruce R. Campell
*Assistant Examiner*—Susan B. McCormick
(74) *Attorney, Agent, or Firm*—Pennie & Edmonds LLP

(57) ABSTRACT

The present invention relates to a new and distinct cultivar of raspberry plant named Driscoll Maravilla. The new cultivar is distinguished from other raspberry cultivars by its fruit firmness, large size, high yield, and long post-harvest life. The new cultivar is distinguished from its seed parent by having larger and firmer fruit. The new cultivar is distinguished from its pollen parent by producing a higher yield of fruit and having shinier, brighter fruit.

3 Drawing Sheets

Latin name of the genus and species of the plant claimed: The variety is botanically identified as *Rubus idaeus L.*

1. BACKGROUND OF THE INVENTION

The new cultivar of raspberry plant was developed from the hybridization of the selection 'Q491.1' (an unpatented variety) as the seed parent with the selection 'Q480.3' (an unpatented variety) as the pollen parent. The parents were crossed in 1996, whereafter fruit and seed were collected to produce seedlings for field planting in Watsonville, Calif. in 1996. The new cultivar was selected from these seedlings in 1998 for its attractiveness and excellent fruit firmness. The new cultivar has been asexually propagated by in vitro shoot tip culture, root sucker division and root cuttings at the Cassin Ranch in Santa Cruz county, Calif. and has been shown to maintain the desired and distinguishing characteristics after propagation over several generations.

2. SUMMARY OF THE INVENTION

The present invention provides a new and distinct cultivar of red raspberry plant named 'Driscoll Maravilla'. The cultivar is botanically identified as *Rubus idaeus L.* The 'Driscoll Maravilla' red raspberry plant produces a primocane crop, which begins in early July and continues until late October. The floricane crop begins in mid-May and continues until late July. Both the primocane and floricane yields are high relative to other comparable varieties. The fruit of 'Driscoll Maravilla' is notably quite firm, large and very consistent with regard to its size and shape throughout its harvest period. The fruit of 'Driscoll Maravilla' separates easily from its receptacle.

3. BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

4. DETAILED BOTANICAL DESCRIPTION

Figure 1:
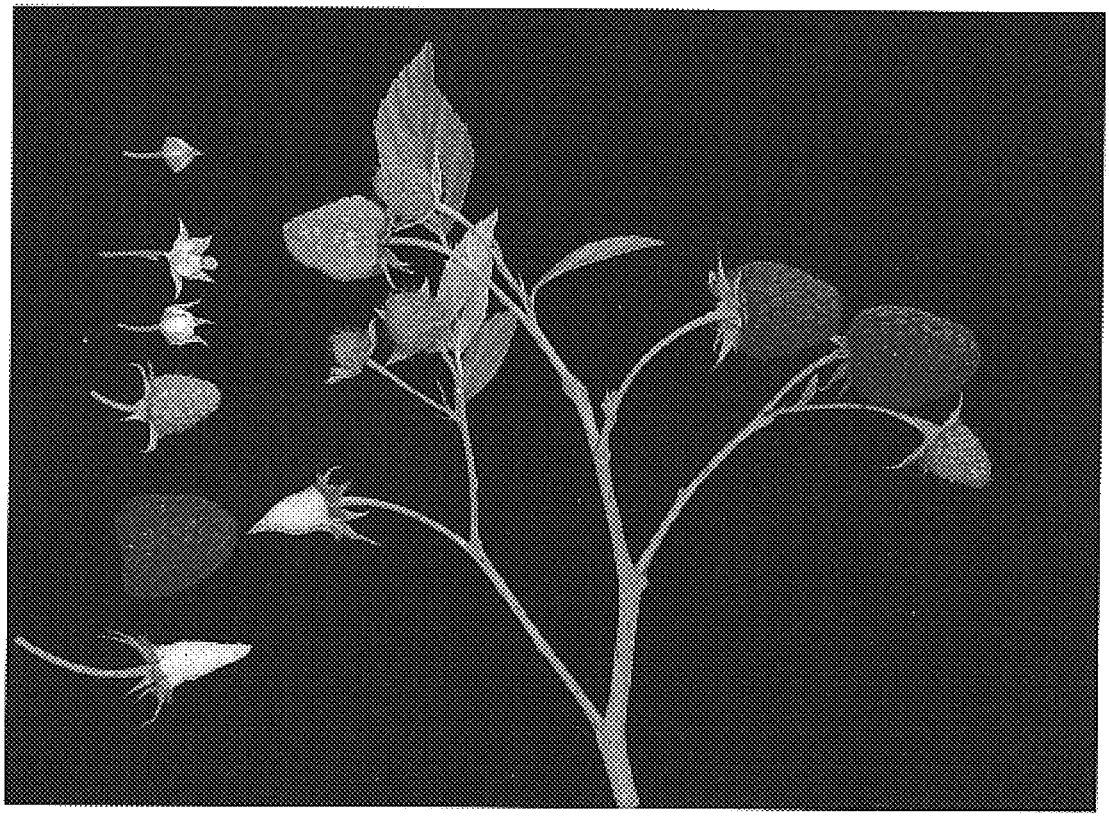
FIG. 1 is a photograph of 'Driscoll Maravilla' primocane flower and fruitin various stages of development.
Figure 2:
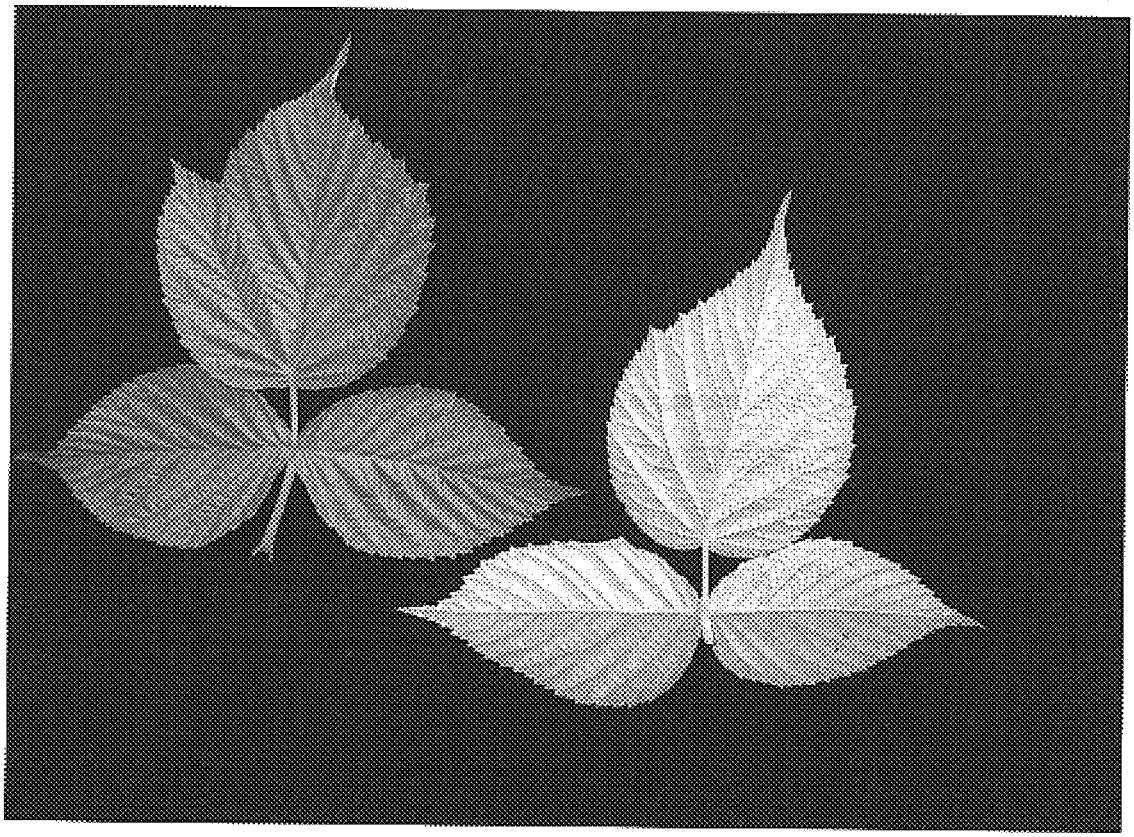
FIG. 2 is a photograph of 'Driscoll Maravilla' primocane leaves showing upper and lower services.
Figure 3:
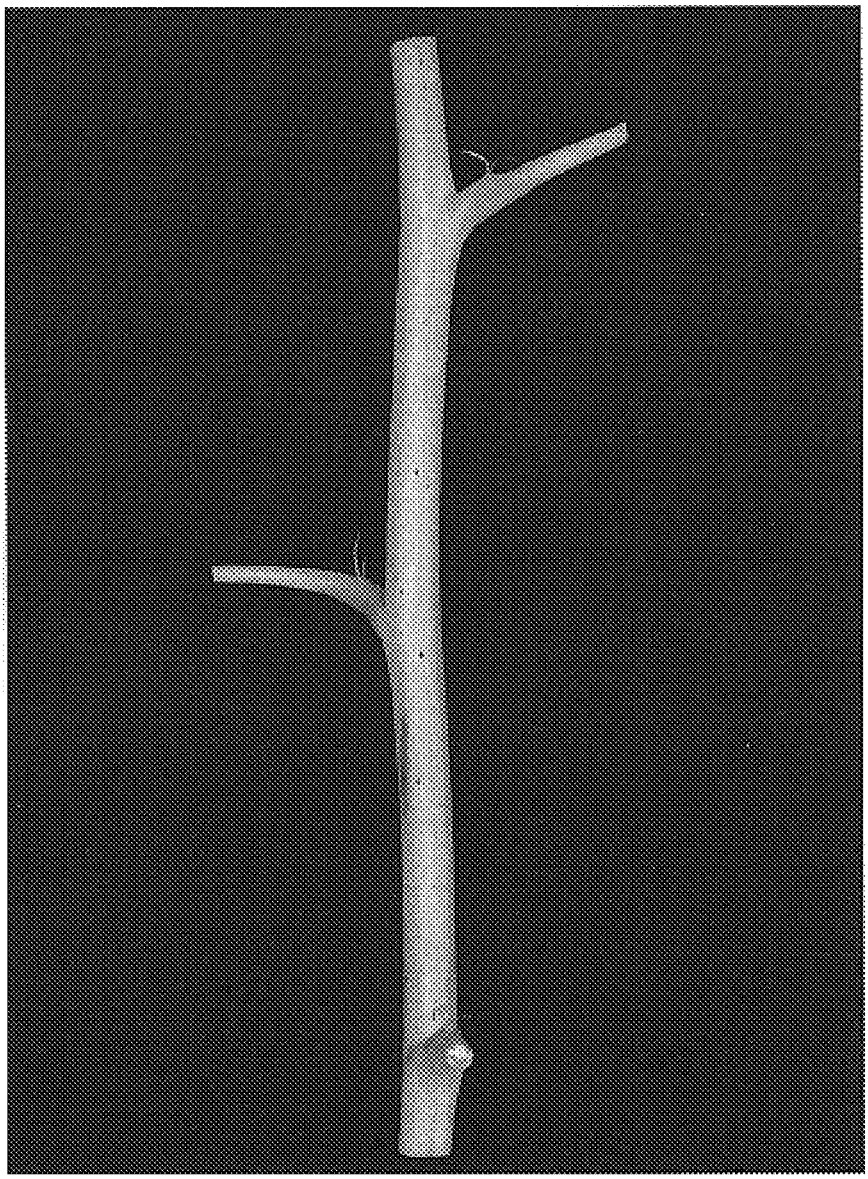
FIG. 3 is a photograph of 'Driscoll Maravilla' primocane shoots.

The following detailed description of the new raspberry cultivar, 'Driscoll Maravilla', is based upon observations taken of 7 to 17 month old plants and fruit grown in Watsonville, Calif. between 2001 and 2002, and is believed to apply to plants of the 'Driscoll Maravilla' cultivar grown in similar conditions of soil and climate elsewhere.

Throughout this specification, color names beginning with a small letter signify that the name of the color, as used in common speech, is aptly descriptive. Color data followed by an alphanumeric code designates the color according to The R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Driscoll Maravilla' compared with characteristics of the unpatented raspberry cultivar 'Heritage'. Observations of the cultivars were taken under similar conditions.

The new variety is particularly characterized and distinguished from other cultivars by its fruit firmness, large size, high yield, and long postharvest life.

The fruit color of 'Driscoll Maravilla' is a bright red at harvest with very little post harvest color change. Fruit of 'Driscoll Maravilla' separates easily from the receptacle and is of excellent firmness at harvest. The fruit of 'Driscoll Maravilla' is very consistent in size and shape throughout the harvest period. The average plant height is about 210 cm and the average plant spread is about 60 cm. The pigmentation of the young shoots is 144B and there were an average of 4 young shoots in the observed plants of 'Driscoll Maravilla'. The prickle pigmentation color is 187A.

The pigmentation color of both surfaces of the petals is 155D and there are five petals per flower. The style pigmentation color is 157D, the average number of styles per flower is about 89, the anther pigmentation color is 155D, and the average number of anthers per flower is about 86. The color of the seeds of 'Driscoll Maravilla' is 161A, the average seed weight is about 1.3 mg, and there are an average of about 83 seeds per fruit.

The primocane and floricane yields of 'Driscoll Maravilla' are high relative to the variety 'Heritage'.

'Driscoll Maravilla' is distinguishable from its pollen parent, selection 'Q480.3', by producing a higher yield of fruit and having shinier, brighter fruit. The new cultivar is distinguished from its seed parent, selection 'Q491.1', by having larger and firmer fruit.

4.1 DISEASE AND STRESS RESISTANCE

Resistance is unknown to powdery mildew. Cold tolerance of the new cultivar has not been established. Post harvest fruit rot resistance is good in comparison over many selections and varieties.

TABLE 1

PLANT CHARACTERISTICS OF 'DRISCOLL MARAVILLA'

| | Driscoll Maravilla | Heritage |
|---|---|---|
| General | | |
| Plant size | Large | Large |
| Growth habit | Semi-erect | Erect |
| Productivity | High | Medium |
| Self-fruitfulness | Self-fruitful | Self-fruitful |
| Time of bud burst | Late | Late |
| Primocane fruiting | | |
| Percent of cane length flowering as primocane | 30-40 | 20-40 |
| Percent of total yield | 44 | 53 |
| Primocanes | | |
| Number of young shoots | Medium | Medium |
| Young shoot pigmentation | Medium | Medium |
| Length (cm) | 231 | 196 |
| Time of shoot emergence | Late | Very late |
| Glaucosity (waxy bloom) | Weak | Weak |
| Strength | Medium | Medium |
| Cane Cross section from mid cane of primocane) | Rounded to angular | Rounded |
| Dormant cane color | tan w/slight purple | brown to purple brown |
| Prickles | | |
| Pigmentation | purple | green-brownish to green |
| Density on young shoots | Medium | Dense |
| Attitude of tip | Horizontal | Downward |
| Size: Length (base to tip at 1 m height at end of season) (mm) | 1.0 | 2.3 |
| Texture | smooth | Rigid |
| Presence and distribution on petioles | Present irregularly distribtuted | Present irregularly distribtuted |
| Pubescence on canes | Absent | Absent |

TABLE 1-continued

PLANT CHARACTERISTICS OF 'DRISCOLL MARAVILLA'

| | Driscoll Maravilla | Heritage |
|---|---|---|
| Internodal distance (cm) (at central ⅓ of cane) | 5.1 | 5.3 |
| LEAVES | | |
| Color | | |
| Face | 147A | 147A |
| Underside | 148C | 148B |
| Relief between veins | Medium | Very weak |
| Glossiness | Medium | Medium |
| Petiole length (cm) | 6.2 | 7.6 |
| Stipule orientation | Erect | Erect |
| Arrangement | Compound | Compound |
| Number of leaflets | Usually 5 | Sometimes 3, sometimes 5 |
| Overlapping of lateral leaflets | Overlapping | Free to touching |
| Lateral leaflet: length of stalket (lower pair) | Medium | Very short |
| Terminal leaflet | | |
| Length (cm) | 11.9 | 14.6 |
| Width (cm) | 8.4 | 7.8 |
| Shape | Ovate | Ovate |
| Tip | Acuminate | Acuminate |
| Base | Round to cordate | Acute to rounded |
| Margin | Doubly serrate | Doubly serrate |
| Lateral leaflets (basal pair) | | |
| Length (cm) | 10.9 | 14.7 |
| Width (cm) | 8.1 | 8.6 |
| Orientation | Opposite | Opposite |
| Shape | Ovate | Ovate |
| Tip | Acuminate | Acuminate |
| Base | Round | Oblique |
| Margin | Doubly serrate | Doubly serrate |
| Rachis length between terminal leaflet and adjacent lateral leaflets (cm) | 3.8 | 1.5 |
| FLOWERS | | |
| Flowering period | | |
| Primocane | 19 weeks, Late May–late September | 19 weeks, Late May–late September |
| Floricane | 12 weeks, Late March–late June | 10 weeks, Late March–mid June |
| Flower diameter (cm) | 1.5 | 1.8 |
| Petal | | |
| Length (cm) | 0.9 | 0.8 |
| Width (cm) | 0.4 | 0.3 |
| Pedicel coloration | Absent | Present, strong intensity |
| FRUIT | | |
| Harvest season | | |
| Primocane | Early July–late October | Early July–early November |
| Floricane | Mid May–mid July | Late May–late July |
| Fruting laterals (floricane) | | |
| Length (4th lateral from tip) (cm) | 60.7 | 49.8 |
| Number of fruit per lateral | 24.6 | 20.3 |
| Color | | |
| Immature | 47C | 42C |
| Maturing | 46A | 46A |
| Mature fruit | 46A | 59A |
| Glossiness | Medium | Medium |
| Shape | Ovate | Ovate |

TABLE 1-continued

| PLANT CHARACTERISTICS OF 'DRISCOLL MARAVILLA' | | |
|---|---|---|
| | Driscoll Maravilla | Heritage |
| Dimensions | | |
| Size | large | small |
| Length (mm) | 22 | 17 |
| Width (mm) | 22 | 18 |
| Length: width | 1.0 | .94 |
| Weight (g/fruit) | | |
| Primocane | 5.5 | 3.1 |
| Floricane | 4.2 | 2.3 |
| Soluble solids (%) | 1.36 | 1.58 |
| Titratable acidity (% as citric acid) | 8.5 | 9.9 |
| Seed Weight (mg) | 2.1 | 1.5 |
| Number druplets/fruit | 83 | 72 |
| Adherence to plug (1–9) | Medium | Medium |
| Firmness | Firm | Firm |
| Yield | High | Medium |

4.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of Driscoll Maravilla and Heritage yielded DNA fragment patterns that uniquely distinguish each of these genetically distinct genotypes.

We claim:

1. A new and distinctive cultivar of raspberry plant, substantially as shown and described.

* * * * *

UNITED STATES PATENT AND TRADEMARK OFFICE

CERTIFICATE OF CORRECTION

PATENT NO. : PP 14, 804 P2 
DATED : May 18, 2004
INVENTOR(S) : Carlos D. Fear, Richard E. Harrison, Fred M. Cook and Gavin Sills It is certified that error appears in the above-identified patent and that said Letters Patent is hereby corrected as shown below:

Column 5,
Line 12, change "1.36" to -- 10.8 --
Line 12, change "1.58" to -- 10.8 --
Line 13, change "8.5" to -- 1.36 --
Line 13, change "9.9" to -- 1.58 --

Signed and Sealed this

First Day of February, 2005

JON W. DUDAS
*Director of the United States Patent and Trademark Office*